United States Patent
McDonnell

(10) Patent No.: US 8,454,644 B2
(45) Date of Patent: Jun. 4, 2013

(54) SWITCHING STICK DILATION METHOD AND APPARATUS

(75) Inventor: Christopher McDonnell, Sandy Hook, CT (US)

(73) Assignee: Stryker Spine (FR)

( * ) Notice: Subject to any disclaimer, the term of this patent is extended or adjusted under 35 U.S.C. 154(b) by 1528 days.

(21) Appl. No.: 11/363,404

(22) Filed: Feb. 27, 2006

(65) Prior Publication Data

US 2006/0229656 A1 Oct. 12, 2006

Related U.S. Application Data

(60) Provisional application No. 60/668,756, filed on Apr. 6, 2005.

(51) Int. Cl.
*A61B 17/00* (2006.01)

(52) U.S. Cl.
USPC .......................................................... 606/190

(58) Field of Classification Search
USPC .. 606/190, 191, 194, 198, 108, 246; 604/264, 604/161, 164, 170.02, 170.01, 164.01, 117; 600/114, 224
See application file for complete search history.

(56) References Cited

U.S. PATENT DOCUMENTS

| 5,976,146 A | 11/1999 | Ogawa et al. |
| 6,159,179 A * | 12/2000 | Simonson ..................... 604/117 |
| 6,371,968 B1 | 4/2002 | Kogasaka et al. |
| 2005/0216002 A1* | 9/2005 | Simonson ..................... 606/61 |

FOREIGN PATENT DOCUMENTS

| EP | 0 890 341 A1 | 1/1999 |
| EP | 1 468 652 A1 | 10/2004 |

* cited by examiner

*Primary Examiner* — Thomas McEvoy
(74) *Attorney, Agent, or Firm* — Lerner, David, Littenberg, Krumholz & Mentlik, LLP

(57) ABSTRACT

A method of dilating an incision to provide access to a surgical site. Such method may include the steps of making an incision in the skin of a patient near a predetermined surgical site, inserting into the incision a dilator, inserting at least one shoe horn in juxtaposition or in direct apposition with the dilator, removing the dilator from the incision, inserting a blunt dissector adjacent the at least one shoe horn, removing the at least one shoe horn, inserting a retractor or a tube over the blunt dissector and into the incision such that the retractor or tube is at or adjacent the predetermined surgical site, removing the blunt dissector from the incision, and performing a surgical procedure at the predetermined surgical site through the retractor or tube.

9 Claims, 3 Drawing Sheets

FIG. 5
FIG. 6
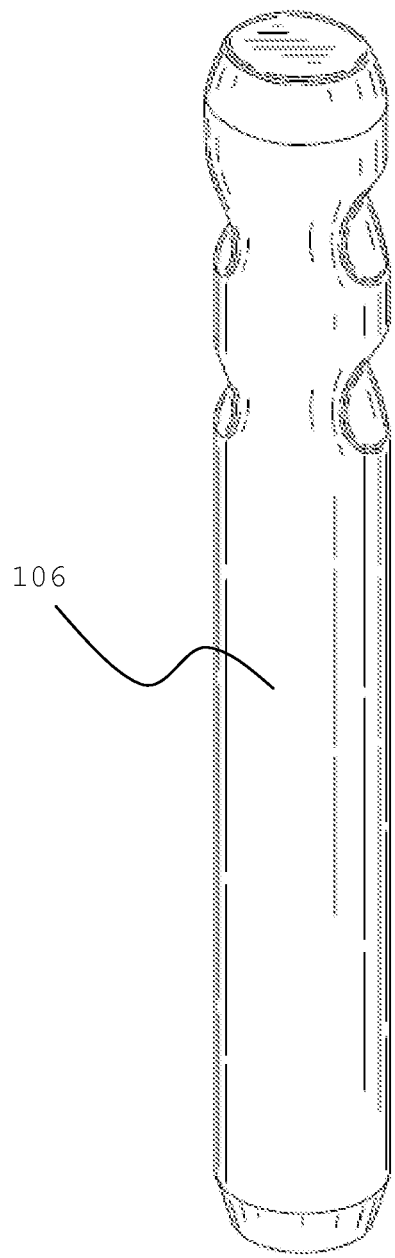
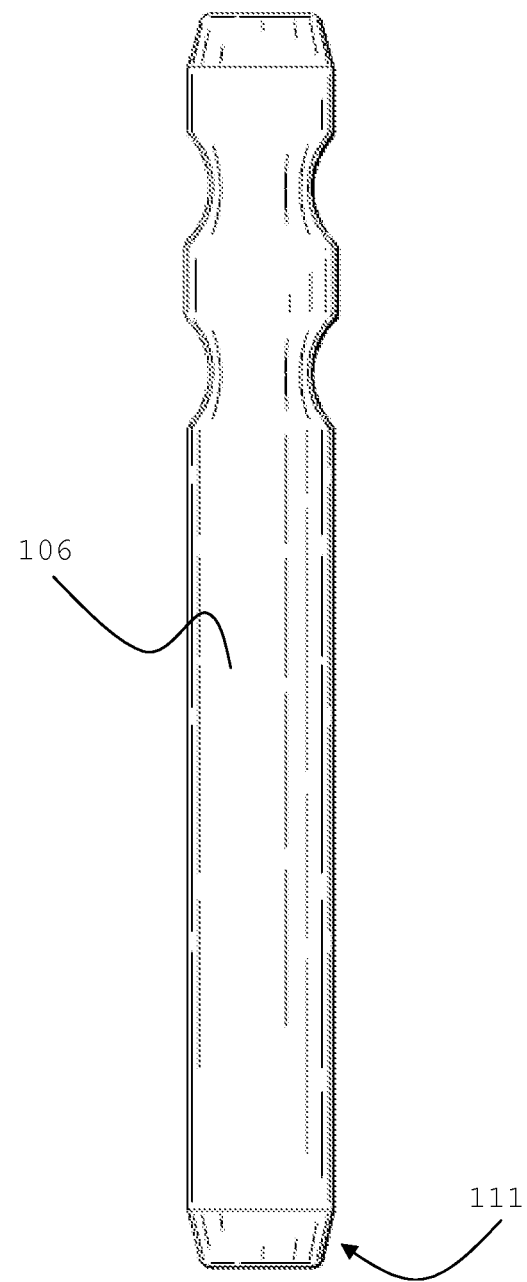
FIG. 7
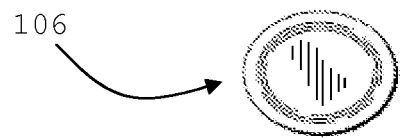

SWITCHING STICK DILATION METHOD AND APPARATUS

CROSS-REFERENCE TO RELATED APPLICATIONS

The present application claims benefit of U.S. Provisional Application No. 60/668,756, filed on Apr. 6, 2005, which is hereby incorporated by reference.

BACKGROUND OF THE INVENTION

The present invention relates to the dilation of a small incision to facilitate introduction of instruments for the performance of surgery.

There is great interest in minimally invasive or less invasive surgery in most surgical procedures because there is believed to be less trauma to the patient and less healing time for the patient than through conventional open procedures. To accomplish the goals of minimally invasive or less invasive surgery, the surgical procedure is preferably conducted through a dilated small incision. Often, a retractor is used within a dilated small incision. The retractor maintains the small incision in a dilated state while a surgeon works through the retractor at the surgical site.

The preliminary procedure of dilating an incision is known and used for spinal surgeries, including static or dynamic stabilization, the insertion of fusion devices, a discectomy, a laminectomy, the insertion of motion preservation devices such as artificial discs, and like devices. Moreover, dilation of small incisions in other surgical procedures are very much applicable to spinal surgery.

The present invention provides an alternative to conventional procedures for dilating a small incision. Gradual dilation of a small incision is facilitated through the use of the present invention.

SUMMARY OF THE INVENTION

The present invention may be reduced to practice through the introduction of a Cobb dilator into a small incision, preferably guided by a K wire. In a preferred embodiment, the Cobb dilator, or the first dilator, is cannulated to receive a K wire, or a pin, as a guide to the surgical site. In another aspect of the present invention, the Cobb dilator need not be cannulated. The surgeon may not need to be guided by a K wire to the surgical site, and thus cannulation would not be required. The introduction of the Cobb dilator is followed by the introduction of a first Kelly retractor, or shoe horn, and then preferably followed by the introduction of a second Kelly retractor, or shoe horn. The Cobb dilator may then be removed and the Kelly retractors manipulated to facilitate entry of a blunt dissector, preferably manifested as a solid tubular component, into the surgical incision between the Kelly retractors. The Kelly retractors may then be removed and a retractor or tubular port may be introduced over the blunt dissector. The blunt dissector can then be removed and the surgical area defined by the retractor blades, or the surgical area defined by a tube, can be accessed by the surgeon in performing a surgical procedure.

A variation of the above method may include the elimination or the Kelly retractors. Thus, a blunt dissector will follow the use of the Cobb dilator without using the Kelly retractors. A retractor or a tube is used in the same manner over the blunt dissector.

Yet another variation on the above methods would be to again eliminate the use of the Kelly retractor or shoe horn, and utilize not one, but two Cobb dilators. The first Cobb dilator could be used in connection with a K wire or pin and then removed from the incision. In the case of using a Cobb dilator with a K wire or pin, the K wire or pin would preferably be removed either together or after the removal of the first Cobb dilator. A second Cobb dilator or other dilator would be introduced into the incision and used to open the muscle towards the surgical site. The second dilator would be larger than the first dilator, and while the second Cobb dilator could be cannulated, it is not necessary if the K wire is removed with the first Cobb dilator. A retractor or a tube would be placed over the second dilator in the same manner as above.

In connection with yet another aspect of the present invention, whether or not the Cobb dilator is cannulated, the blunt dissector may be cannulated, wherein the cannulation in the blunt dissector is large enough to accept the Cobb dilator. Thus, in connection with this aspect of the present invention, the Cobb dilator will not need to be removed before the insertion of the blunt dissector. This preserves the surgical trajectory as identified by the Cobb dilator, and K wire, if used. Again, in connection with this latter concept, the present invention contemplates either using Kelly retractors to manipulate and gradually dilate the incision or to go forward without using the Kelly retractors. If Kelly retractors are utilized, the Kelly retractors may be removed prior to the introduction of the blunt dissector. However, the cannulated blunt dissector may be introduced over the Cobb dilator with the Kelly retractors, or at least one Kelly retractor, in place. This may facilitate protection of the tissue as the cannulated blunt dissector is introduced over the Cobb dilator.

BRIEF DESCRIPTION OF THE DRAWINGS

FIG. 5 is a perspective view of a blunt dissector.

FIG. 6 is a front elevational view of a blunt dissector in accordance with the present invention, shown without cannulation.

FIG. 7 is a bottom plan view of the blunt dissector shown in FIG. 5.

DETAILED DESCRIPTION OF THE INVENTION

Figure 1:
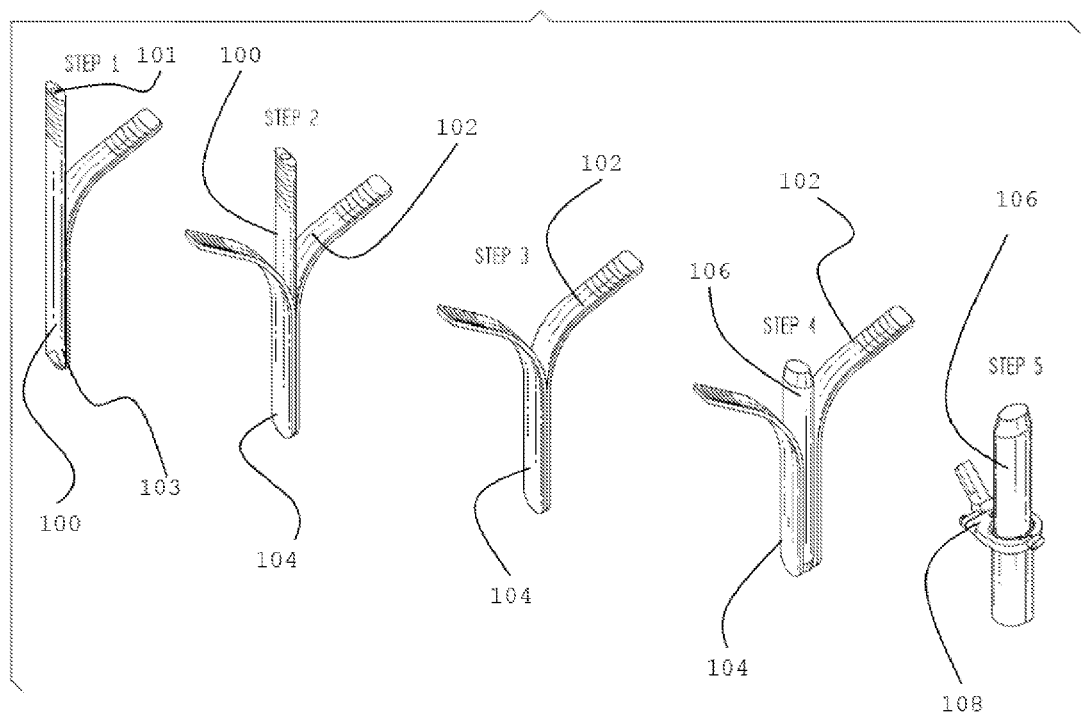
FIG. 1 is a perspective view showing the steps of the present invention in accordance with one embodiment of the present invention.

FIG. 1 shows the progression of certain steps taken in connection with the use of the Cobb dilator 100, Kelly retractors 102 and 104 (or shoe horns), blunt dissector 106, and retractor 108. Not shown is the conventional step of utilizing a K wire or pin to identify a surgical site and guide the Cobb dilator 100 into the surgical site.

It is also noted that the retractor 108 shown in step 5 of FIG. 1 can be of any suitable type as selected by the surgeon. The retractor shown is an expandable retractor, wherein blades attached to a collar can be expanded so that the access through the retractor can be made progressively wider towards the surgical site. A non-expandable retractor may be used, or a tube may be used, depending upon surgeon preference and the type of surgery to be undertaken.

The retractor shown in FIG. 1 is disclosed in U.S. Pat. No. 7,182,729, filed on Sep. 17, 2004, entitled "Surgical Retractor With Removable Scissor Arms." Another retractor is disclosed in U.S. Provisional Application No. 60/642,234, filed on Jan. 7, 2005, entitled "Three-Prong Retractor With Elastomer Sheath." These applications and their disclosures are incorporated by reference herein as if fully set forth herein. In particular, the types of surgical procedures disclosed and claimed in such applications are incorporated herein by reference as if fully set forth herein as the same are applicable to the methods and apparatus in accordance with the present invention.

In FIG. 1, the Cobb dilator 100 is cannulated such that it includes a bore 101 that will receive a K wire or a pin (not shown). The Cobb dilator 100 is preferably an elongate oval shape in cross-section. The insertion end 103 preferably includes a rounded profile or tapered profile along the elongate axis of the cross-section, thus facilitating smooth introduction and avoiding damage to tissue during introduction.

Figure 2:
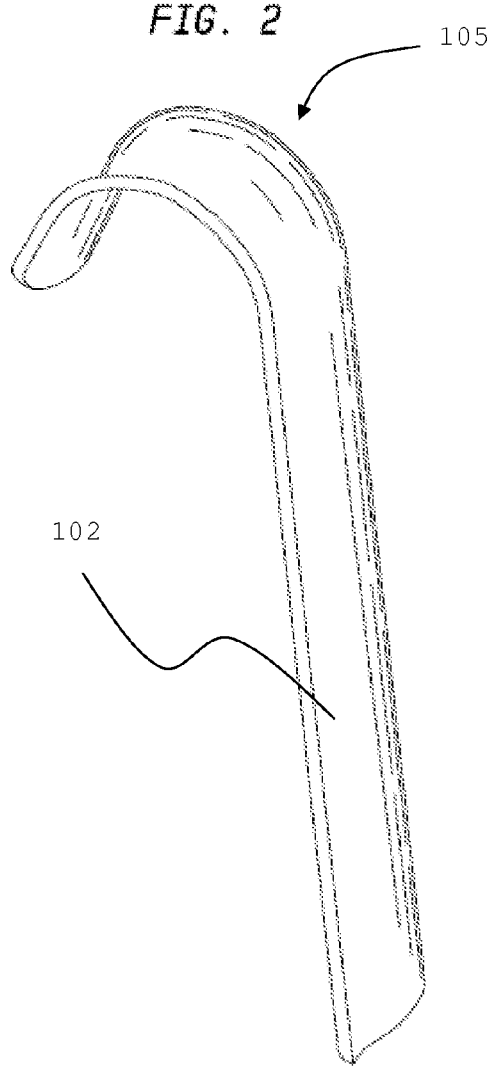
FIG. 2 is a perspective view of a Kelly retractor or shoe horn.
Figure 3:
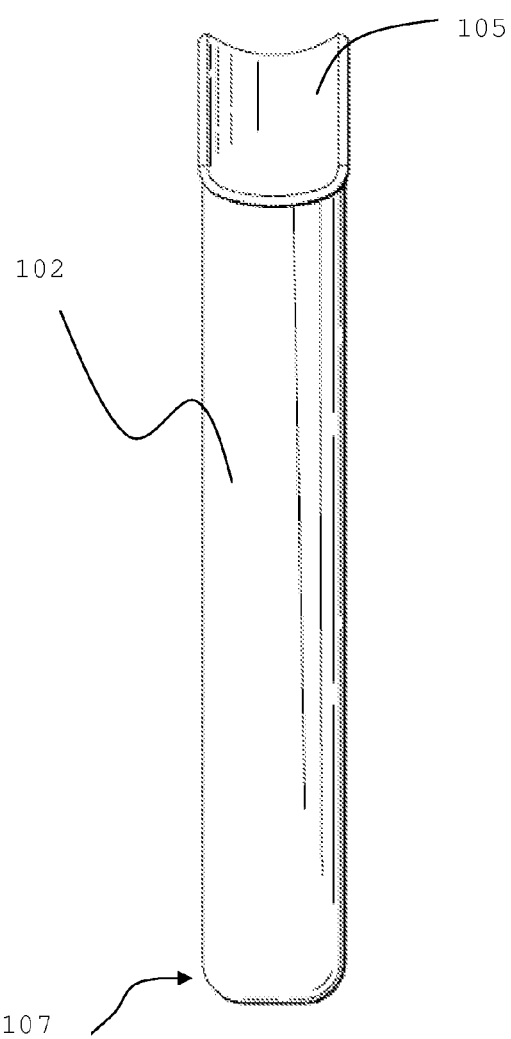
FIG. 3 is a front elevational view of the Kelly retractor shown in FIG. 2.
Figure 4:
FIG. 4 is a bottom plan view of the Kelly retractor shown in FIG. 3.

The Kelly retractors 102 and 104 (or shoe horns) are shown in FIGS. 1-4, each Kelly retractor 102 and 104 being substantially similar in configuration. In FIG. 2, a perspective view reveals the contour of the Kelly retractor 102, with a somewhat more curvate trailing end 105 than that shown in FIG. 1. The Kelly retractors 102 and 104 are arcuate in cross-section, as shown in FIG. 4. FIG. 3 reveals the rounded insertion end 107. The insertion end 107 of the Kelly retractor 102 may also include a somewhat tapered or rounded profile as shown in FIG. 3. Such a tapering or rounded profile may only be necessary on the exterior side 109, or arcuate side, of the Kelly retractor 102. This can be seen in FIG. 1 at the insertion of the Kelly retractors 102 and 104 depicted in steps 1 and 2.

FIGS. 5, 6, and 7 show the blunt dissector 106 in accordance with an embodiment of the present invention. FIGS. 5-7 reveal an elongate tubular shape of the blunt dissector 106, together with a tapered insertion end 111, which again facilitates insertion and avoids damage to tissue as the blunt dissector 106 is being introduced. Of course, any suitable shape can be incorporated into the cross-section of the blunt dissector 106, though it is preferable that it have some operational relationship to the shape of the Kelly retractors 102 and 104 (or shoe horns) so that introduction is not impeded, and is preferably facilitated. FIG. 7 reveals the cross-sectional shape of the blunt dissector 106 as an oval shape. This oval exterior shape coincides with the interior shape of the retractor 108 in accordance with one embodiment of the present invention.

The blunt dissector 106 shown in FIG. 5 is not cannulated, but may be cannulated for purposes of sliding over the Cobb dilator 100. The lines shown on FIGS. 6 and 7 for the top portion of FIG. 5 may also represent cannulation, though the cannulation in the blunt dissector 106 is preferably shaped to accept the Cobb dilator 100, in which case it would be a narrow oval shape for the illustrated embodiment, or whatever other shape the Cobb dilator 100 takes on in accordance with any embodiment of the present invention.

FIG. 6 also reveals arcuate depressions at the end of the trailing end of the blunt dissector 106. These arcuate depressions are four in number, and are aligned diametrically opposite one another. These arcuate depressions facilitate the handling of the blunt dissector 106 by the surgeon.

With respect to the method in accordance with the present invention, reference is made to steps 1-5 of FIG. 1. The progression of steps in connection with this particular disclosed embodiment begins at the left upper corner and progresses through the steps toward the right bottom corner. The steps illustrated are not exclusive.

A small incision is made in the patient's skin near the surgical site. Preferably, a K wire or a pin is inserted to the surgical site, or adjacent the surgical site. This step is conventional and is not depicted in FIG. 1. In step 1, a Cobb dilator 100, which is cannulated, is inserted over the K wire or the pin (not shown). A Kelly retractor 102 (or shoe horn) is inserted on one side of the Cobb dilator 100, preferably with matching surfaces in juxtaposition with one another, or in direct apposition with one another. Preferably, a second Kelly retractor 104 (or shoe horn) is inserted on the opposite side of the Cobb dilator 100, as shown in step 2. The Kelly retractors 102 and 104, or shoe horns, are then used to manipulate the tissue to gradually dilate the small incision. Prior to, during, or after the manipulation of the tissue by the Kelly retractors 102 and 104, the Cobb dilator 100 is removed, as shown in step 3.

In step 4, it can be seen that the blunt dissector 106 is inserted between the Kelly retractors 102 and 104 (or shoe horns). Once the blunt dissector 106 has been sufficiently inserted into the skin incision, such that it is at or near the surgical site, the Kelly retractors 102 and 104 can be removed. The small incision has now been gradually dilated to the size of the blunt dissector 106. The retractor 108, as shown in step 5 of FIG. 1, is placed over the blunt dissector 106 and into the surgical wound. The blunt dissector 106 can now be removed and the retractor 108 can be used by the surgeon as the surgeon sees fit. This can include the expansion of the retractor 108.

Surgical procedures such as those described in the above referenced patent applications can now be performed by the surgeon.

There are many variations to the method in accordance with the present invention, some of which are described above.

While the foregoing description and figures illustrate preferred embodiments of the shoe horn dilation method and apparatus in accordance with the present invention, it should be appreciated that certain modifications can be made, and are encouraged to be made in the structure, materials, and techniques of the disclosed embodiments without departing from the spirit and scope of the present invention which is intended to be captured by the overall reading of the present application, and in particular, that set forth in the Summary of the Invention, as well as the claims in general, as set forth below.

What is claimed is:

1. A method of dilating an incision to provide access to a surgical site, including the steps of:

making an incision in the skin of a patient near a predetermined surgical site, inserting into the incision a dilator, inserting a first shoe horn in juxtaposition or in direct apposition with a first side of the dilator, inserting a second shoe horn in juxtaposition or in direct apposition with a second side of the dilator, the second side being opposite the first side, removing the dilator from the incision after the steps of inserting the first and second shoe horns, inserting a blunt dissector between the first and second shoe horns after the step of removing the dilator, removing the first and second shoe horns, inserting a retractor or a tube over the blunt dissector and into the incision such that the retractor or tube is at or adjacent the predetermined surgical site, removing the blunt dissector from the incision, and performing a surgical procedure at the predetermined surgical site through the retractor or tube.

2. The method of claim 1, wherein the step of inserting the blunt dissector includes manipulating the first and second shoe horns to further dilate the tissue.

3. The method of claim 1, wherein at least one of the first and second shoe horns is arcuately shaped.

4. The method of claim 1, wherein the blunt dissector is inserted in a space vacated by the dilator.

5. A method of dilating an incision to provide access to a surgical site, including the steps of:
- making an incision in the skin of a patient near a predetermined surgical site,
- inserting into the incision a dilator,
- inserting a first shoe horn in juxtaposition or in direct apposition with a first side of the dilator,
- inserting a second shoe horn in juxtaposition or in direct apposition with a second side of the dilator, the second side being opposite the first side,
- removing the dilator from the incision,
- inserting a blunt dissector adjacent the first and second shoe horns,
- moving the first shoe horn apart from the second shoe horn to dilate the tissue during the insertion of the blunt dissector,
- removing the first and second shoe horns,
- inserting a retractor or a tube over the blunt dissector and into the incision such that the retractor or tube is at or adjacent the predetermined surgical site,
- removing the blunt dissector from the incision, and
- performing a surgical procedure at the predetermined surgical site through the retractor or tube.

6. The method of claim 5, wherein the step of inserting the blunt dissector includes inserting the blunt dissector between the first and second shoe horns.

7. The method of claim 5, wherein at least one of the first and second shoe horns is arcuately shaped.

8. The method of claim 5, wherein at least one of the first and second shoe horns is shaped along a portion of an oval.

9. The method of claim 5, wherein the blunt dissector is inserted in a space vacated by the dilator.

\* \* \* \* \*